(12) United States Patent
Delmotte et al.

(10) Patent No.: US 12,090,244 B2
(45) Date of Patent: Sep. 17, 2024

(54) SURGICAL ADHESIVE ABLE TO GLUE IN WET CONDITIONS

(71) Applicants: Baxter International Inc., Deerfield, IL (US); Baxter Healthcare SA, Glattpark (CH)

(72) Inventors: Yves A. Delmotte, Neufmaison (BE); Jonathan Payssan, Uccle (FR)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 350 days.

(21) Appl. No.: 17/525,095

(22) Filed: Nov. 12, 2021

(65) Prior Publication Data
US 2022/0072195 A1   Mar. 10, 2022

Related U.S. Application Data

(63) Continuation of application No. 15/914,210, filed on Mar. 7, 2018, now Pat. No. 11,202,848.

(60) Provisional application No. 62/468,563, filed on Mar. 8, 2017.

(51) Int. Cl.
| | |
|---|---|
| *A61M 5/19* | (2006.01) |
| *A61B 17/03* | (2006.01) |
| *A61L 24/00* | (2006.01) |
| *A61L 24/04* | (2006.01) |

(52) U.S. Cl.
CPC ........... *A61L 24/043* (2013.01); *A61L 24/001* (2013.01); *A61L 24/046* (2013.01); *A61L 2400/04* (2013.01); *A61L 2400/06* (2013.01)

(58) Field of Classification Search
CPC ...... A61M 3/005; A61M 5/19; A61M 5/2448; A61M 5/3294; A61B 17/00491; A61B 2017/00504; A61B 2017/00495; A61L 24/043; A61L 2400/04; B65D 51/2864
USPC ............ 604/82, 83, 191, 218; 606/213, 214; 424/78.17; 222/135, 137, 145.6; 206/219–221, 363–364, 438
See application file for complete search history.

(56) References Cited

U.S. PATENT DOCUMENTS

| | | | |
|---|---|---|---|
| 4,359,049 A | 11/1982 | Redl et al. | |
| 4,631,055 A | 12/1986 | Redl et al. | |
| 4,978,336 A * | 12/1990 | Capozzi ............ | B05C 17/00593 604/82 |
| 5,015,677 A | 5/1991 | Benedict et al. | |
| 5,116,315 A | 5/1992 | Capozzi et al. | |
| 5,328,955 A | 7/1994 | Rhee et al. | |
| 5,585,007 A | 12/1996 | Antanavich et al. | |
| 5,814,066 A * | 9/1998 | Spotnitz ............ | A61B 17/00491 128/898 |
| 6,312,725 B1 | 11/2001 | Wallace et al. | |
| 6,454,786 B1 | 9/2002 | Holm et al. | |
| 6,461,325 B1 | 10/2002 | Delmotte et al. | |
| 6,534,591 B2 | 3/2003 | Rhee et al. | |
| 6,624,245 B2 | 9/2003 | Wallace et al. | |
| 6,911,496 B2 | 6/2005 | Rhee et al. | |
| 7,208,171 B2 | 4/2007 | Messersmith et al. | |
| 7,575,131 B2 * | 8/2009 | Feinberg ............... | B01F 31/441 604/82 |
| 7,622,533 B2 | 11/2009 | Lee | |
| 7,727,547 B2 | 6/2010 | Fortune et al. | |
| 8,029,774 B2 | 10/2011 | Beckman et al. | |

(Continued)

*Primary Examiner* — Luan K Bui
(74) *Attorney, Agent, or Firm* — K&L Gates LLP

(57) ABSTRACT

Compositions and methods for sealing tissue of a patient in a wet environment are disclosed.

15 Claims, 5 Drawing Sheets

(56) References Cited

U.S. PATENT DOCUMENTS

| | | |
|---|---|---|
| 8,067,031 B2 | 11/2011 | Daniloff et al. |
| 8,383,092 B2 | 2/2013 | Lee et al. |
| 8,409,602 B2 | 4/2013 | Messersmith et al. |
| 8,460,708 B2 | 6/2013 | Daniloff et al. |
| 8,481,073 B2 | 7/2013 | Daniloff et al. |
| 8,512,749 B2 | 8/2013 | Sawhney et al. |
| 8,673,286 B2 | 3/2014 | Messersmith et al. |
| 8,791,219 B2 | 7/2014 | Grubbs et al. |
| 8,846,849 B2 | 9/2014 | Bordoloi et al. |
| 8,916,652 B2 | 12/2014 | Dalsin et al. |
| 9,114,172 B2 | 8/2015 | Rhee et al. |
| 9,115,289 B2 | 8/2015 | Lee et al. |
| 2003/0087338 A1 | 5/2003 | Messersmith et al. |
| 2004/0068266 A1 | 4/2004 | Delmotte |
| 2005/0201974 A1 | 9/2005 | Schestopol et al. |
| 2006/0071025 A1 | 4/2006 | Crews |
| 2008/0247984 A1 | 10/2008 | Messersmith et al. |
| 2009/0163845 A1 | 6/2009 | Meyer-Ingold |
| 2012/0016390 A1 | 1/2012 | Lee et al. |
| 2012/0041481 A1* | 2/2012 | Daniloff ............... A61K 9/1647 606/214 |
| 2012/0116424 A1 | 5/2012 | Lee et al. |
| 2013/0172823 A1* | 7/2013 | Meron ............. A61B 17/00491 604/506 |
| 2015/0094689 A1* | 4/2015 | Steffen ............. A61B 17/00491 604/518 |
| 2018/0256775 A1 | 9/2018 | Delmotte et al. |

* cited by examiner

FIG. 2

SURGICAL ADHESIVE ABLE TO GLUE IN WET CONDITIONS

CROSS-REFERENCE TO RELATED APPLICATIONS

This application is a continuation of U.S. patent application Ser. No. 15/914,210, filed on Mar. 7, 2018, which claims the benefit of Provisional Application No. 62/468,563, filed on Mar. 8, 2017, the entire contents of each of which are expressly incorporated herein by reference.

FIELD OF THE DISCLOSURE

The disclosure relates generally to surgical adhesives and sealants. More particularly, the disclosure relates to surgical adhesives and sealants suitable for application to wet surfaces.

BACKGROUND

Surgeons are routinely required to achieve hemostasis and stop both minor and massive bleeding, particularly of highly vascularized organs. Organs are naturally wet to facilitate their motion and reduce friction, and are further wetted during surgery due to extracorporeal fluids that are produced and use of irrigation solutions to aspirate debris, clear the field of view, and avoid adhesion formation. However, bonding to wet tissue surfaces is difficult to achieve. Current surgical adhesives and sealants often lack sufficient ability to adhere to wet surfaces.

SUMMARY

The present disclosure is directed to compositions and methods for sealing tissue of a patient under wet conditions.

In one aspect, the present disclosure provides a kit comprising: (a) a dry powder composition comprising a first component having a polymer core substituted with at least two sulfhydryl groups and a second component having a polymer core substituted with at least two sulfhydryl-reactive groups; (b) a first aqueous solution comprising L-3,4-dihydroxyphenylalanine (L-DOPA) and having a pH of about 1 to about 5.5; and (c) a second aqueous solution having a pH of about 6 to about 11; wherein each of (a), (b), and (c) is packaged separately prior to use.

In another aspect, the disclosure provides a composition comprising a crosslinked polymeric material having a structure:

wherein each n is independently 15 to 150; and each m is independently 15 to 150.

In another aspect, the disclosure provides a composition prepared by reacting a component having a polymer core substituted with at least two sulfhydryl-reactive groups with (i) L-DOPA and (ii) a component having a polymer core substituted with at least two sulfhydryl groups.

In another aspect, the disclosure provides a kit comprising: (a) a dry powder composition comprising a first component having a polymer core substituted with at least two sulfhydryl groups and a second component having a polymer core substituted with at least two sulfhydryl-reactive groups; (b) a first aqueous solution having a pH of about 1 to about 5.5; (c) a second aqueous solution having a pH of about 6 to about 11; and (d) L-3,4-dihydroxyphenylalanine (L-DOPA); wherein each of (a), (b), (c), and (d) is packaged separately prior to use.

In another aspect, the disclosure provides a method of sealing tissue of a patient comprising: (a) dissolving a dry powder composition comprising a first component having a polymer core substituted with at least two sulfhydryl groups and a second component having a polymer core substituted with at least two sulfhydryl-reactive groups in a first aqueous solution comprising L-3,4-dihydroxyphenylalanine (L-DOPA) and having a pH of about 1 to about 5.5 to form a homogeneous solution; (b) adding a second aqueous solution having a pH of about 6 to about 11 to the homogeneous solution to form a mixture; and (c) placing the mixture into contact with a tissue surface and allowing a three-dimensional composition to form on the tissue.

In another aspect, the disclosure provides a method of sealing tissue of a patient comprising: (a) treating a tissue surface with a solution of L-DOPA to obtain a treated tissue surface; (b) dissolving a dry powder composition comprising a first component having a polymer core substituted with at least two sulfhydryl groups and a second component having a polymer core substituted with at least two sulfhydryl-reactive groups in a first aqueous solution having a pH of about 1 to about 5.5 to form a homogeneous solution; (c) adding a second aqueous solution having a pH of about 6 to about 11 to the homogeneous solution to form a mixture; and (d) placing the mixture into contact with the treated tissue surface and allowing a three-dimensional composition to form on the treated tissue surface.

The foregoing summary is not intended to define every aspect of the disclosure, and other features and advantages of the present disclosure will become apparent from the following detailed description. The present disclosure is

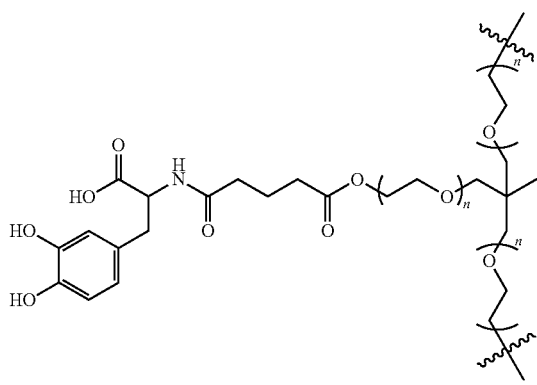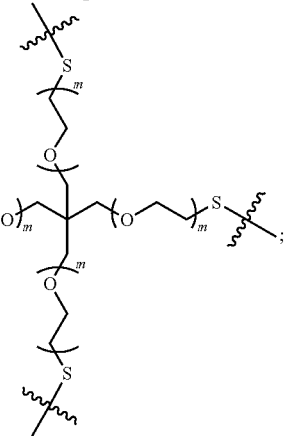

intended to be related as a unified document, and it should be understood that all combinations of features described herein are contemplated, even if the combination of features are not found together in the same sentence, paragraph, or section of this disclosure. In addition, the disclosure includes, as an additional aspect, all embodiments of the disclosure narrower in scope in any way than the variations specifically mentioned above. With respect to aspects of the disclosure described or claimed with "a" or "an," it should be understood that these terms mean "one or more" unless context unambiguously requires a more restricted meaning. With respect to elements described as one or more within a set, it should be understood that all combinations within the set are contemplated. If aspects of the disclosure are described as "comprising" a feature, embodiments also are contemplated "consisting of" or "consisting essentially of" the feature. Additional features and variations of the disclosure will be apparent to those skilled in the art from the entirety of this application, and all such features are intended as aspects of the disclosure.

BRIEF DESCRIPTION OF THE DRAWINGS

FIG. 2 is a schematic drawing showing the 2×2 matrix defined for application of Coseal® surgical sealant (Baxter International) with DOPA ("Coseal DOPA (+)") and Coseal® surgical sealant without DOPA ("Coseal DOPA (−)") onto wet and dry surfaces.

DETAILED DESCRIPTION

Figure 1A:
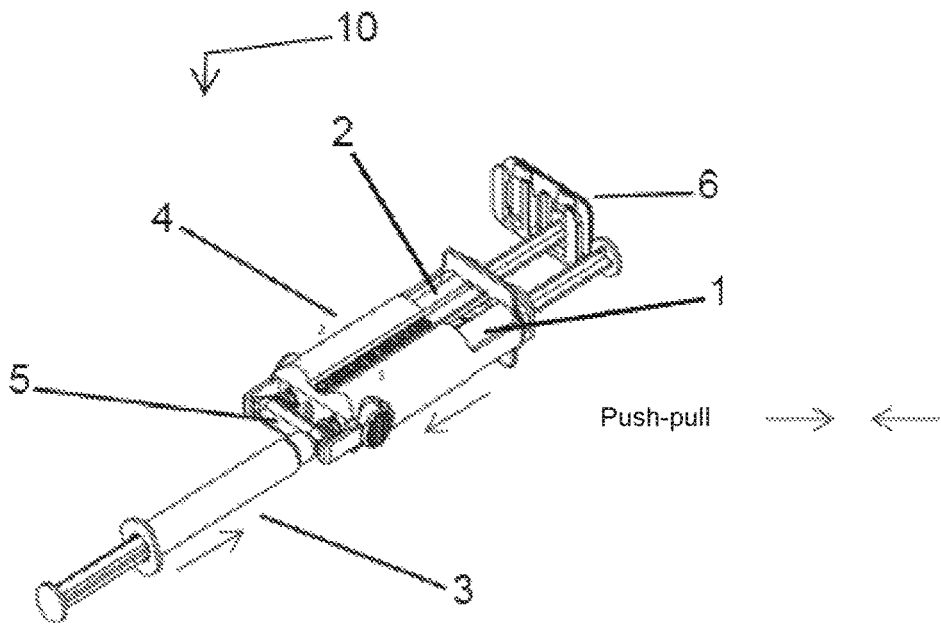
FIG. 1A shows a representative multi-compartment syringe device for generating and delivering a surgical sealant and adhesive composition according to the disclosure.

The present disclosure provides surgical adhesives and sealants suitable for application to wet surfaces. Surgical adhesives and sealants are described, for example, in U.S. Pat. Nos. 6,312,725, 6,624,245, 6,911,496, 8,067,031, 8,460,708, and 8,481,073, which are hereby incorporated by reference in their entireties.

The surgical adhesives and sealants disclosed herein including L-DOPA advantageously demonstrated adhesion to both dry and wet surfaces. In particular, the surgical adhesives and sealants disclosed herein demonstrate improved adhesion to wet surfaces as compared to a surgical adhesive or sealant that does not contain L-DOPA.

Dry Powder Composition

The present disclosure provides a dry powder composition that contains at least two biocompatible, non-immunogenic components having reactive groups thereon, with the functional groups selected so as to enable reaction between the components, i.e., crosslinking, to form a three-dimensional matrix. Each component has a polymer core substituted with reactive groups. The dry powder composition contains a first component having a polymer core substituted with nucleophilic groups (e.g., amino groups or thiol groups) and a second component having a polymer core substituted with electrophilic groups (e.g., succinimidyl groups). Dry powder compositions having more than two components also are encompassed, where additional components may have nucleophilic or electrophilic groups.

The reactive groups are selected so that the components are essentially non-reactive in a dry environment, for example, when the component having a polymer core substituted with nucleophilic groups and the component having a polymer core substituted with electrophilic groups are formulated as and/or provided as a homogeneous dry powder. Upon exposure to an aqueous environment, the components are rendered reactive and a plurality of components are then able to react in the aqueous environment to form a three-dimensional matrix. This matrix is preferably formed without input of any external energy, for example, at room temperature or at slightly elevated temperature.

The composition is particularly suitable for application involving contact between a biological system and the composition and/or the three-dimensional matrix formed therefrom. The biological system can be a biological tissue, and in a preferred embodiment, is living tissue.

The resulting three-dimensional matrix is useful in a variety of contexts, and is particularly useful as a biomaterial for medical applications, such as for bioadhesion, tissue augmentation, tissue sealing, vascular sealing, needle hole sealing, hemostasis, and the prevention of adhesions following a surgical procedure or injury, for example.

In one embodiment, substantially immediately or immediately upon exposure to the aqueous environment, the reactive groups on the components of the composition begin to react and form a three-dimensional matrix. The term "substantially immediately" is intended to mean within less than five minutes, preferably within less than two minutes, and the term "immediately" is intended to mean within less than one minute, preferably within less than 30 seconds. Typically, the three-dimensional composition will be completely formed within about 30 minutes.

The homogeneous dry powder composition is comprised of: a first component having a polymeric core substituted with nucleophilic groups (e.g., amino groups or thiol groups) and a second component having a polymeric core substituted with electrophilic groups (e.g., succinimidyl groups). The nucleophilic and electrophilic groups are non-reactive with one another when the first and second components are admixed in a dry environment but are rendered reactive upon exposure to an aqueous environment such that the components react in the aqueous environment to form a three-dimensional matrix. In some cases, the nucleophilic and electrophilic groups are relatively non-reactive with one another in an aqueous environment having an acidic pH, but are rendered reactive upon exposure to an aqueous environment having a basic pH. In order for a three-dimensional matrix to be formed, there is a plurality of reactive groups present in each of the first and second components. In a preferred embodiment, one component has a polymeric core substituted with two or more (e.g., 3, 4, 5, 6, 7, or 8) nucleophilic groups, and the other component has a polymeric core substituted with two or more (e.g., 3, 4, 5, 6, 7, or 8) electrophilic groups. The homogeneous dry powder composition optionally includes L-DOPA.

The selection of electrophilic groups provided on the second component is made so that reaction is possible with the specific nucleophilic groups on the first component. Thus, when the nucleophilic groups are sulfhydryl moieties, the electrophilic groups are selected so as to react with sulfhydryl moieties. Suitable sulfhydryl-reactive groups include, but are not limited to, mixed anhydrides; ester derivatives of phosphorus; ester derivatives of p-nitrophenol, p-nitrothiophenol and pentafluorophenol; esters of substituted hydroxylamines, including N-hydroxyphthalimide esters, N-hydroxysuccinimide esters, N-hydroxysulfosuccinimide esters, and N-hydroxyglutarimide esters; esters of 1-hydroxybenzotriazole; 3-hydroxy-3,4-dihydro-benzotriazin-4-one; 3-hydroxy-3,4-dihydro-quinazoline-4-one; carbonylimidazole derivatives; acid chlorides; ketenes; isocyanates; maleimides; substituted maleimides; haloalkanes; epoxides; imines; aziridines; olefins (including conjugated olefins) such as ethenesulfonyl, etheneimino, acrylate, methacrylate, and α,β-unsaturated aldehydes and ketones; and combinations thereof.

Examples of sulfhydryl-reactive groups include, but are not limited to,

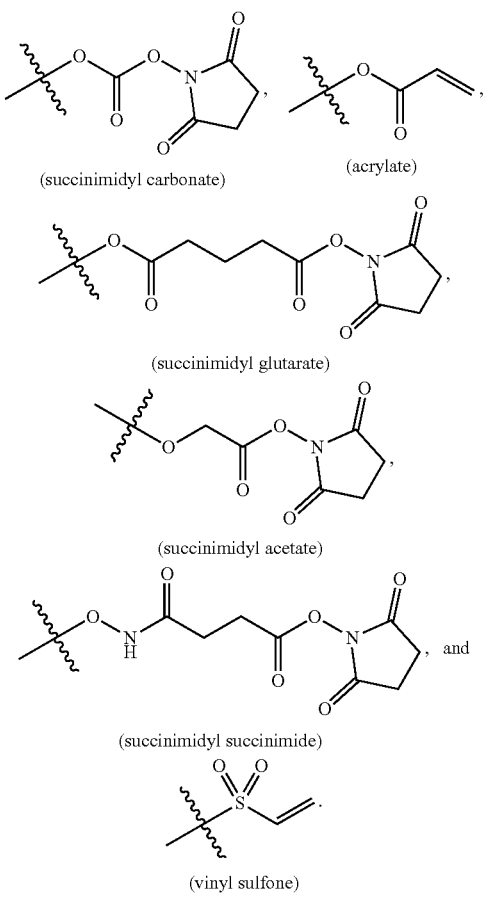

(succinimidyl carbonate) (acrylate)

(succinimidyl glutarate)

(succinimidyl acetate)

(succinimidyl succinimide) , and (vinyl sulfone)

The polymer core of each component comprises a polymer to which the reactive groups are bound. Suitable polymers include, but are not limited to, polyalkylene oxides, particularly polyethylene glycol (PEG) and poly(ethylene oxide)-poly(propylene oxide) copolymers, including block and random copolymers; polyols such as glycerol, polyglycerol (PG), particularly highly branched polyglycerol, and propylene glycol; poly(oxyalkylene)-substituted diols, and poly(oxyalkylene)-substituted polyols such as mono-, di- and tri-polyoxyethylated glycerol, mono- and di-polyoxyethylated propylene glycol, and mono- and di-polyoxyethylated trimethylene glycol; polyoxyethylated sorbitol, polyoxyethylated glucose; poly(acrylic acids) and analogs and copolymers thereof, such as polyacrylic acid per se, polymethacrylic acid, poly(hydroxyethylmethacrylate), poly (hydroxyethylacrylate), poly(methylalkylsulfoxide methacrylates), poly(methylalkylsulfoxide acrylates) and copolymers of any of the foregoing, and/or with additional acrylate species such as aminoethyl acrylate and mono-2-(acryloxy)-ethyl succinate; polymaleic acid; poly(acrylamides) such as polyacrylamide per se, poly(methacrylamide), poly(dimethylacrylamide), poly(N-isopropyl-acrylamide), and copolymers thereof; poly(olefinic alcohols) such as poly(vinyl alcohols) and copolymers thereof; poly(N-vinyl lactams) such as poly(vinyl pyrrolidones), poly(N-vinyl caprolactams), and copolymers thereof; polyoxazolines, including poly(methyloxazoline) and poly(ethyloxazoline); and polyvinylamines; as well as copolymers of any of the foregoing.

Those of ordinary skill in the art will appreciate that synthetic polymers such as polyethylene glycol cannot be prepared practically to have exact molecular weights, and that the term "molecular weight" as used herein refers to the weight average molecular weight of a number of molecules in any given sample, as commonly used in the art. Thus, a sample of PEG 2,000 might contain a statistical mixture of polymer molecules ranging in weight from, for example, 1,500 to 2,500 daltons with one molecule differing slightly from the next over a range. Specification of a range of molecular weights indicates that the average molecular weight may be any value between the limits specified, and may include molecules outside those limits. Thus, a molecular weight range of about 800 to about 20,000 indicates an average molecular weight of at least about 800, ranging up to about 20 kDa.

Although a variety of different polymers can be used in the present compositions, as indicated above, preferred synthetic hydrophilic polymers are PEG and PG, particularly highly branched PEG. Various forms of PEG are extensively used in the modification of biologically active molecules because PEG lacks toxicity, antigenicity, and immunogenicity (i.e., is biocompatible), can be formulated so as to have a wide range of solubilities, and does not typically interfere with the enzymatic activities and/or conformations of peptides. A particularly preferred polymer for certain applications is a PEG having a molecular weight within the range of about 100 to about 100,000, although for highly branched PEG, far higher molecular weight polymers can be employed, up to 1,000,000 or more, providing that biodegradable sites are incorporated ensuring that all degradation products will have a molecular weight of less than about 30,000. For most PEGs, however, the preferred molecular weight is about 1,000 to about 20,000, more preferably within the range of about 7,500 to about 20,000. Most preferably, the polyethylene glycol has a molecular weight of approximately 10,000.

Multi-functionalized forms of PEG are of particular interest and include, but are not limited to, PEG succinimidyl glutarate, PEG succinimidyl propionate, PEG succinimidyl butylate, PEG succinimidyl acetate, PEG succinimidyl succinamide, PEG succinimidyl carbonate, PEG propionaldehyde, PEG glycidyl ether, PEG-isocyanate, and PEG-vinylsulfone. Many such forms of PEG are described in U.S. Pat. Nos. 5,328,955 and 6,534,591, which are hereby incorporated by reference in their entireties. Various forms of multi-amino PEG are commercially available from sources such as PEG Shop, a division of SunBio of South Korea (www.sunbio.com), Nippon Oil and Fats (Yebisu Garden Place Tower, 20-3 Ebisu 4-chome, Shibuya-ku, Tokyo), Nektar Therapeutics (San Carlos, Calif., formerly Shearwater Polymers, Huntsville, Ala.) and from Huntsman's Performance Chemicals Group (Houston, Tex.) under the name Jeffamine® polyoxyalkyleneamines. Multi-amino PEGs include the Jeffamine® diamines ("D" series) and triamines ("T" series), which contain two and three primary amino groups per molecule. Poly(sulfhydryl) PEGs are available from Nektar Therapeutics, e.g., in the form of pentaerythritol poly(ethylene glycol) ether tetra-sulfhydryl (molecular weight 10,000). Various forms of multi-arm (e.g., 4-, 6-, and 8-arm) PEG also are commercially available from sources such as Creative PEGWorks (Chapel Hill, N.C.) and Sigma-Aldrich (St. Louis, Mo.).

In an embodiment, the first component polymer core and second component polymer core are both branched poly (ethylene oxide). In an embodiment, the first component polymer core and second component polymer core are both 4-arm poly(ethylene oxide). In an embodiment, the first component polymer core and second component polymer core are both 8-arm poly(ethylene oxide). In an embodiment, the first component polymer core and second component polymer core are independently 4-arm poly(ethylene oxide), 6-arm poly(ethylene oxide), and/or 8-arm poly(ethylene oxide). In an embodiment, the sulfhydryl-reactive groups are succinimidyl groups. In an embodiment, the dry powder composition comprises a 4-arm, succinimidyl-terminated poly(ethylene oxide) and a 4-arm, thiol-terminated poly(ethylene oxide). In an embodiment, the dry powder composition comprises an 8-arm, succinimidyl-terminated poly(ethylene oxide) and an 8-arm, thiol-terminated poly(ethylene oxide). In an embodiment, the dry powder composition comprises an 8-arm, succinimidyl-terminated poly(ethylene oxide) and a 4-arm, thiol-terminated poly(ethylene oxide). In an embodiment, the dry powder composition comprises a 4-arm, succinimidyl-terminated poly(ethylene oxide) and an 8-arm, thiol-terminated poly(ethylene oxide).

In an embodiment, the first component is

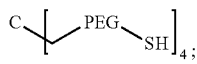

wherein PEG is poly(ethylene oxide). Each PEG independently includes a number of ethylene oxide units, for example, 15 to 150, 30 to 100, 35 to 90, 40 to 80, 45 to 70, 50 to 60, 54 to 58, 20 to 40, 40 to 60, 50 to 80, and/or 80 to 130 ethylene oxide units.

In an embodiment, the second component is

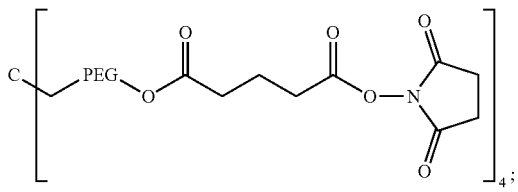

wherein PEG is poly(ethylene oxide). Each PEG independently includes a number of ethylene oxide units, for example, 15 to 150, 30 to 100, 35 to 90, 40 to 80, 45 to 70, 50 to 60, 54 to 58, 20 to 40, 40 to 60, 50 to 80, and/or 80 to 130 ethylene oxide units.

In an embodiment, the 4-arm, succinimidyl-terminated poly(ethylene oxide) has a weight average molecular weight (Mw) of about 8 kDa to about 14 kDa, such as about 9 kDa to about 13 kDa, about 10 kDa to about 12 kDa, and/or about 11 kDa. In an embodiment, the 4-arm, thiol-terminated poly(ethylene oxide) has a weight average molecular weight (Mw) of about 7 kDa to about 13 kDa, such as about 8 kDa to about 12 kDa, 9 kDa to about 11 kDa, and/or about 10 kDa.

Formation of the Three-Dimensional Matrix

A three-dimensional matrix is formed by: (a) providing a first component having a polymeric core substituted with nucleophilic groups (e.g., amino groups or thiol groups), a second component having a polymeric core substituted with electrophilic groups (e.g., succinimidyl groups), and L-DOPA; (b) rendering the nucleophilic and electrophilic groups reactive by exposing the first component, second component, and L-DOPA to an aqueous environment having a pH sufficient to effect reaction; and (c) allowing a three-dimensional matrix to form. Typically, the matrix is formed, e.g., by polymerization, without input of any external energy.

In one embodiment, a three-dimensional matrix is formed by: (a) dissolving a dry powder composition comprising a first component having a polymer core substituted with at least two sulfhydryl groups and a second component having a polymer core substituted with at least two sulfhydryl-reactive groups in a first aqueous solution comprising L-3,4-dihydroxyphenylalanine (L-DOPA) and having a pH of about 1 to about 5.5 to form a homogeneous solution; (b) adding a second aqueous solution having a pH of about 6 to about 11 to the homogeneous solution to form a mixture; and (c) placing the mixture into contact with a tissue surface and allowing a three-dimensional composition to form on the tissue surface.

In one embodiment, a three-dimensional matrix is formed by: (a) treating a tissue surface with a solution of L-DOPA to obtained a treated tissue surface; (b) dissolving a dry powder composition comprising a first component having a polymer core substituted with at least two sulfhydryl groups and a second component having a polymer core substituted with at least two sulfhydryl-reactive groups in a first aqueous solution having a pH of about 1 to about 5.5 to form a homogeneous solution; (c) adding a second aqueous solution having a pH of about 6 to about 11 to the homogeneous solution to form a mixture; and (d) placing the mixture into contact with the treated tissue surface and allowing a three-dimensional composition to form on the treated tissue surface.

The first and second components of the dry powder composition are typically combined in amounts such that the number of nucleophilic groups (e.g., amino groups or thiol groups) in the mixture is approximately equal to the number of electrophilic groups (e.g., succinimidyl groups) in the mixture. As used in this context, the term "approximately" refers to a 2:1 to 1:2 ratio of moles of nucleophilic groups to moles of electrophilic groups. A 1:1 molar ratio of nucleophilic to electrophilic groups is generally preferred.

The first and second components are blended together to form a homogeneous dry powder. This powder is then combined with an aqueous solution having a pH within the range of about 1.0 to 5.5, such as about 1.2 to about 5, about 1.4 to about 4.5, about 1.5 to about 4, about 1.6 to about 3.5, about 1.7 to about 3, about 1.8 to about 2.7, about 1.9 to about 2.5, about 2 to about 2.4, and/or about 2.1 to about 2.3, to form a homogeneous acidic aqueous solution, and this solution is then combined with an aqueous solution having a pH within the range of about 6.0 to 11.0, such as about 7 to about 10.5, such as about 8 to about 10, about 9 to about 10, about 9.3 to about 10, about 9.5 to about 9.9, about 9.6 to about 9.8, about 9.65 to about 9.75, and/or about 9.7, to form a reactive solution.

The acidic aqueous solutions having a pH within the range of about 1.0 to 5.5, include by way of illustration and not limitation, solutions of: citric acid, hydrochloric acid, phosphoric acid, sulfuric acid, 3-[(1,1-dimethyl-2-hydroxyethyl)amino]-2-hydroxypropanesulfonic acid (AMPSO), acetic acid, lactic acid, and combinations thereof. In a preferred embodiment, the acidic aqueous solution is a solution of citric acid, hydrochloric acid, phosphoric acid, sulfuric acid, and combinations thereof.

Regardless of the precise acidifying agent, the acidic solution preferably has a pH such that it retards the reactivity of the nucleophilic groups on the first component. For example, a pH of 2.1 is generally sufficient to retard the nucleophilicity of thiol groups. An exemplary acidic solution is a solution of hydrochloric acid, having a concentration of about 6.3 mM and a pH in the range of 2.1 to 2.3. This solution may be prepared by combining concentrated hydrochloric acid with water, i.e., by diluting concentrated hydrochloric acid with water.

Basic aqueous solutions having a pH within the range of about 6.0 to 11.0, include by way of illustration and not limitation, solutions of: glutamate, acetate, carbonate and carbonate salts (e.g., sodium carbonate, sodium carbonate monohydrate and sodium bicarbonate), borate, phosphate and phosphate salts (e.g., monobasic sodium phosphate monohydrate and dibasic sodium phosphate), and combinations thereof. In a preferred embodiment, the basic aqueous solution is a solution of carbonate salts, phosphate salts, and combinations thereof.

In general, the basic solution is an aqueous solution that neutralizes the effect of the acidic solution, when it is added to the homogeneous solution of the first and second components and the acid solution, so that the nucleophilic groups of the first component regain their nucleophilic character (that has been masked by the action of the acidic solution), thus allowing the nucleophilic groups to react with the electrophilic groups of the second component. An exemplary basic solution is an aqueous solution of carbonate and phosphate salts, e.g., sodium phosphate and sodium carbonate.

In an embodiment, the three-dimensional matrix comprises a crosslinked polymeric material having a structure:

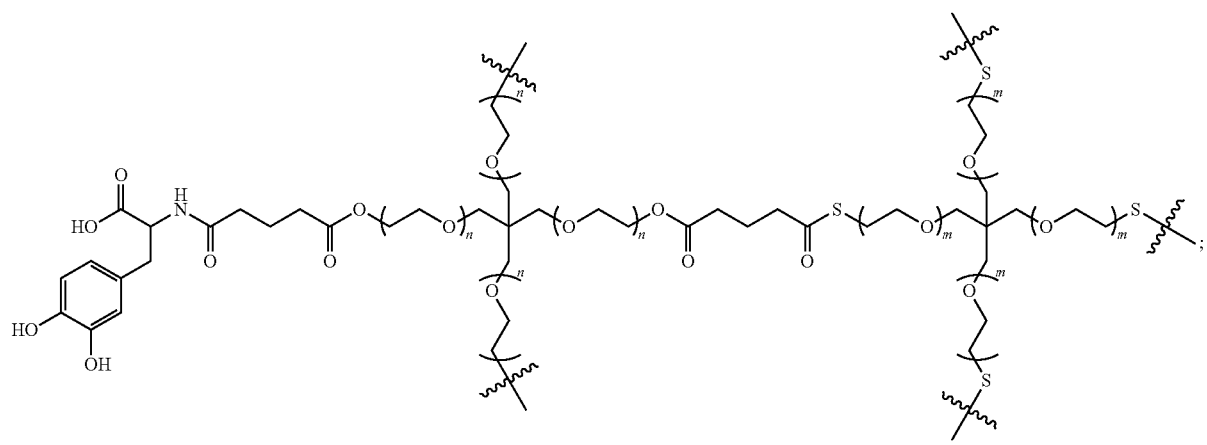

wherein each n is independently 15 to 150, 30 to 100, 35 to 90, 40 to 80, 45 to 70, 50 to 60, 54 to 58, 20 to 40, 40 to 60, 50 to 80, and/or 80 to 130; and each m is independently 15 to 150, 30 to 100, 35 to 90, 40 to 80, 45 to 70, 50 to 60, 54 to 58, 20 to 40, 40 to 60, 50 to 80, and/or 80 to 130. In the formula above, use of the symbol ∿ indicates that the molecular structure beyond this point is unspecified crosslinked material generally formed by reaction of the first component, the second component, and L-DOPA as described herein. The formula above is a representative example of a structure generally formed by reaction of a 4-arm, sulfhydryl-reactive group-terminated poly(ethylene oxide), a 4-arm, thiol-terminated poly(ethylene oxide), and L-DOPA as described herein.

In an embodiment, the three-dimensional matrix comprises a crosslinked polymeric material having a structure:

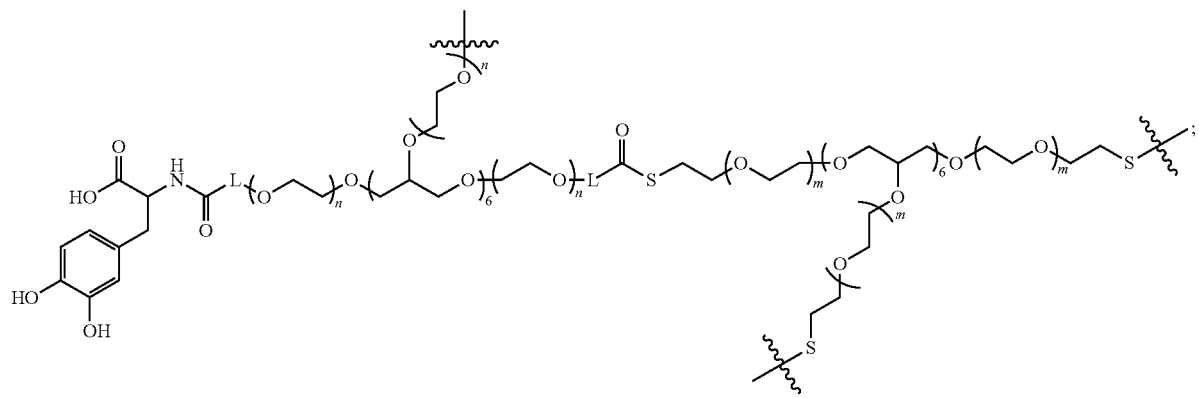

wherein L is null, —(CH$_2$)$_{1-5}$—, —CO(CH$_2$)$_{1-5}$—, —NHCO(CH$_2$)$_{1-5}$—, or —(CH$_2$)$_{1-5}$NHCO(CH$_2$)$_{1-5}$—; each n is independently 15 to 150, 20 to 40, 40 to 60, 50 to 80, and/or 80 to 130; and each m is independently 15 to 150, 20 to 40, 40 to 60, 50 to 80, and/or 80 to 130. In the formula above, use of the symbol ⁓ indicates that the molecular structure beyond this point is unspecified crosslinked material generally formed by reaction of the first component, the second component, and L-DOPA as described herein. The formula above is a representative example of a structure generally formed by reaction of an 8-arm, sulfhydryl-reactive group-terminated poly(ethylene oxide), an 8-arm, thiol-terminated poly(ethylene oxide), and L-DOPA as described herein.

In an embodiment, the three-dimensional matrix comprises a crosslinked polymeric material having a structure:

second component, and L-DOPA as described herein. The formula above is a representative example of a structure generally formed by reaction of an 8-arm, sulfhydryl-reactive group-terminated poly(ethylene oxide), an 8-arm, thiol-terminated poly(ethylene oxide), and L-DOPA as described herein.

In an embodiment, the three-dimensional matrix is prepared by reacting a component having a polymer core substituted with at least two (e.g., 3, 4, 5, 6, 7, or 8) sulfhydryl-reactive groups with (i) L-DOPA and (ii) a component having a polymer core substituted with at least two (e.g., 3, 4, 5, 6, 7, or 8) sulfhydryl groups.

Delivery Systems

Multi-Compartment Devices: Suitable delivery systems for the homogeneous dry powder composition and the two aqueous solutions may involve a multi-compartment device,

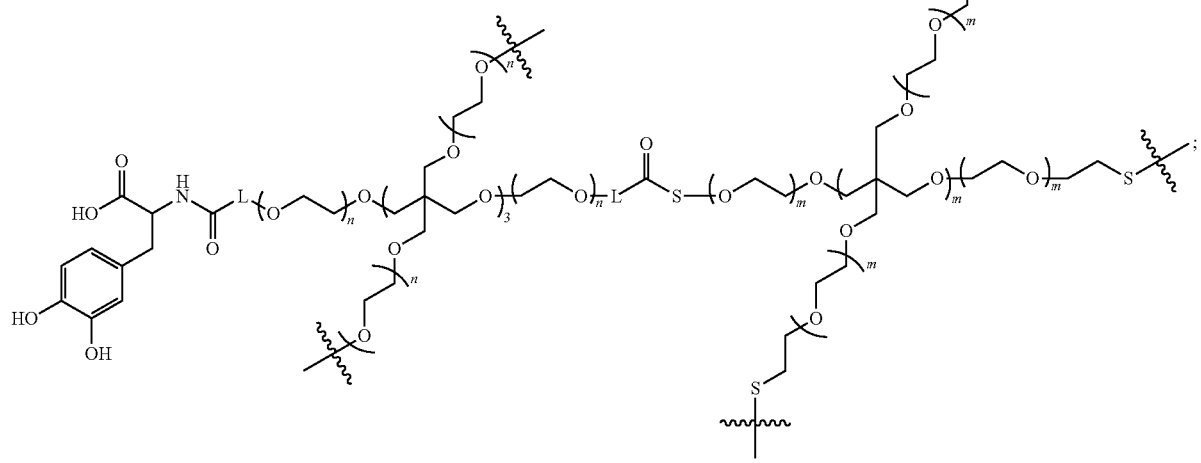

wherein L is null, —(CH$_2$)$_{1-5}$—, —CO(CH$_2$)$_{1-5}$—, —NHCO(CH$_2$)$_{1-5}$—, or —(CH$_2$)$_{1-5}$NHCO(CH$_2$)$_{1-5}$—; each n is independently 15 to 150, 20 to 40, 40 to 60, 50 to 80, and/or 80 to 130; and each m is independently 15 to 150, 20 to 40, 40 to 60, 50 to 80, and/or 80 to 130. In the formula above, use of the symbol ⁓ indicates that the molecular structure beyond this point is unspecified crosslinked material generally formed by reaction of the first component, the where one or more compartments contain the powder and one or more compartments contain the aqueous solutions needed to provide for the aqueous environment, such that the dry powder composition can be exposed to the aqueous environment as it leaves its respective compartment. Many devices that are adapted for delivery of multi-component tissue sealants/hemostatic agents are well known in the art and can also be used. Alternatively, the dry powder composition can be delivered using any type of controllable extrusion system, or it can be delivered manually in the form of a dry powder, and exposed to the aqueous environment at the site of administration.

The homogeneous dry powder composition and the two aqueous solutions may be conveniently formed under aseptic conditions by placing each of the three ingredients (dry powder, acidic solution and basic solution) into separate syringe barrels. For example, the dry powder composition, first aqueous solution and second aqueous solution can be housed separately in a multiple-compartment syringe system having multiple syringe barrels, a mixing head, and an exit orifice. The first aqueous solution can be added to the syringe barrel housing the dry powder composition to dissolve the dry powder composition and form a homogeneous solution, which is then extruded into the mixing head. The second aqueous solution can be simultaneously extruded into the mixing head. Finally, the resulting composition can then be extruded through the orifice onto a surface.

For example, the syringe barrels holding the dry powder and the basic solution may be part of a dual-syringe system, e.g., a double barrel syringe as described in U.S. Pat. No. 4,359,049, which is hereby incorporated by reference in its entirety. In this embodiment, the acid solution can be added to the syringe barrel that also holds the dry powder, so as to produce the homogeneous solution. In other words, the acid solution may be added (e.g., injected) into the syringe barrel holding the dry powder to thereby produce a homogeneous solution of the first and second components. This homogeneous solution can then be extruded into a mixing head, while the basic solution is simultaneously extruded into the mixing head. Within the mixing head, the homogeneous solution and the basic solution are mixed together to thereby form a reactive mixture. Thereafter, the reactive mixture is extruded through an orifice and onto a surface (e.g., tissue), where a film is formed, which can function as a sealant or a barrier, or the like. The reactive mixture begins forming a three-dimensional matrix immediately upon being formed by the mixing of the homogeneous solution and the basic solution in the mixing head. Accordingly, the reactive mixture is preferably extruded from the mixing head onto the tissue very quickly after it is formed so that the three-dimensional matrix forms on, and is able to adhere to, the tissue.

Figure 1B:
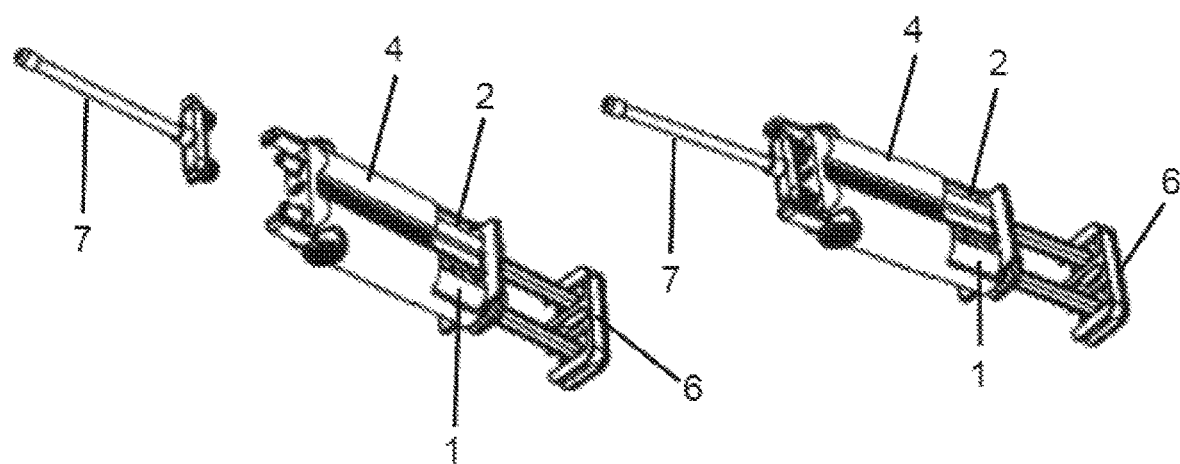
FIG. 1B shows the representative multi-compartment syringe device of FIG. 1A in further combination with an applicator for delivering the surgical sealant and adhesive composition to a site, for example, a biological tissue, where the composition is needed.

A preferred embodiment of a multi-compartment syringe system is shown in FIG. 1A. As shown, the device is comprised of three syringes, with first and second syringes 1, 2 of the multi-compartment syringe device 10 containing the two aqueous solutions and the third syringe 3 containing the dry powder composition. The two syringes 1, 2, containing the solutions are pre-assembled into a syringe housing 4 with a transfer port closure adapter 5 attached to the housing assembly 4 to allow mixing of the dry powder into the correct syringe. A syringe clip 6 can be uncoupled from one of the syringes and remain attached to the plunger rod of the syringe that does not require mixing with the dry powder composition, so as to facilitate separate, independent movement of a plunger (and thus the contents) of the first syringe 1. In this embodiment, the acid solution (with or without L-DOPA) contained in the first syringe 1 is injected into the syringe barrel 3 holding the dry powder to thereby produce a homogeneous solution of the first and second components, and optionally L-DOPA. As shown in FIG. 1A, the syringe clip 6 can be coupled to both of the syringe plungers of the first and second syringes 1, 2, so as to facilitate substantially simultaneous flow of the homogeneous solution contained in the first syringe 1 and the basic solution contained in the second syringe 2 into a mixing head to thereby form a reactive mixture. The reactive mixture can then be delivered via an orifice onto a surface (e.g., tissue), where a film capable of functioning as a sealant, adhesive, barrier, or the like, can be formed. As shown in FIG. 1B, the empty third syringe 3 can be detached from the first syringe 1 and an applicator 7 attached onto the end of the syringe housing 4. Suitable delivery devices include the delivery devices currently used to deliver Coseal® surgical sealant compositions as shown in the packaging insert for this product.

Other systems for combining two reactive liquids are well known in the art, and include the systems described in U.S. Pat. Nos. 6,454,786, 6,461,325, 5,585,007, 5,116,315, and 4,631,055; and U.S. Patent Application Publication No. 2004/0068266, each of which is hereby incorporated by reference in its entirety.

Pressurized Delivery Devices: Other delivery systems for dispensing the multicomponent compositions disclosed herein may include pressurized delivery devices, examples of which are described in U.S. Patent Application Publication No. 2006/0071025, which is hereby incorporated by reference in its entirety. Such a pressurized delivery device may include a diffuser surface having an outlet extending therethrough that is positioned downstream from a plurality of inlets. While at least one inlet is adapted to communicate with a source of a pressurized carrier fluid, each of a plurality of inlets is adapted to communicate with a source of a different fluid component. Using this device, the dry powder solution is premixed with the first acidic aqueous solution, in some embodiments as described above the first acidic solution may further contain L-DOPA, to form a homogeneous solution as previously described and this solution is subsequently communicated as a first fluid component. The second alkaline aqueous buffer solution as described above is communicated as the second fluid component. Once the diffuser surface receives fluid components from the inlets, each received fluid component is pushed toward the outlet for mixing and dispensing therethrough by the pressurized carrier fluid, typically a gas such as air, from the carrier fluid inlet. The diffuser surface and the inlets may represent components of a mixing nozzle.

In general, there are two categories of gas enhanced nozzles for dispensing reactive components of a multicomponent composition—those that involve internal mixing and those that involve external mixing. When the diffuser surface is a part of a nozzle, the nozzle may be considered an internal-mixing nozzle. Unlike other internal-mixing technologies, the internal-mixing nozzle of the pressurized delivery device disclosed herein provides several features that serve individually and collectively to eliminate clogging. For example, a diffuser surface typically has a shape effective to direct and maintain each received fluid component in a different flow path on the diffuser surface toward the outlet for mixing therein and dispensing therethrough. Due to the minimal residence time of the mixture within the nozzle, reactive components do not have time to set and clog the nozzle before the mixture is forced out of the nozzle by the pressurized carrier fluid. In addition, the outlet may be aligned with any or all of the carrier fluid inlets that may be present in the nozzle to direct the pressurized carrier fluid in a manner that enhances fluid component mixing and to expel the mixture in a jet like manner. As the orientation of the diffuser surface relative to the inlets affects the performance of the device, the diffuser surface may be permanently affixed or immobilized with respect to the inlets; however, when the diffuser surface is detachable from the inlets, the nozzle may be disassembled to facilitate cleaning and/or replacement of parts. For example, the diffuser surface may be replaceable/and or disposable. Additionally, when the pressurized delivery device disclosed herein has a diffuser surface that is detachable from the inlets, the device may be constructed to allow assembly of the components in only configurations that align the diffuser surface to the inlets such that the performance of the device is optimized.

Kits

The compositions disclosed herein can be packaged in kits and used in a variety of medical applications. The kit would include aqueous solutions, as well as written or otherwise illustrated instructions for use. A typical kit for use in medical applications, comprises: (a) a homogeneous dry powder composition comprised of: (i) a first component having a polymer core substituted with at least two sulfhydryl groups; and (ii) a second component having a polymer core substituted with at least two sulfhydryl-reactive groups; (b) a first aqueous solution comprising L-3,4-dihydroxyphenylalanine (L-DOPA) and having a pH of about 1 to 5.5; and (c) a second aqueous solution having a pH of about 6 to 11; wherein each component is packaged separately and admixed immediately prior to use. As is evident to those of ordinary skill in the art, prior to use, each component should be packaged separately such that the component remains sterile and does not contact another component. As an example, two of the individual components can be packaged in separate sterile packages such as separate syringe barrels of a multiple-compartment syringe system having multiple syringe barrels as described above.

Another typical kit for use in medical applications, comprises: (a) a dry powder composition comprised of: (i) a first component having a polymer core substituted with at least two sulfhydryl groups; and (ii) a second component having a polymer core substituted with at least two sulfhydryl-reactive groups; (b) a first aqueous solution having a pH of about 1 to about 5.5; (c) a second aqueous solution having a pH of about 6 to about 11; and (d) L-3,4-dihydroxyphenylalanine (L-DOPA); wherein each component is packaged separately such that the component remains sterile and does not contact another component. In an embodiment, L-DOPA is provided as a powder. In an embodiment, L-DOPA is provided as an aqueous solution, such as a pre-filled syringe or a vial As is evident to those of ordinary skill in the art, prior to use, each component should remain in a separate sterile package.

In another embodiment, the kit further comprises a delivery system that will allow the surgical sealant and/or adhesive composition to be delivered as a spray. The spray can be generated by manually mixing the components and passing them through a spray nozzle. The spray generation can also be accomplished by using a flow of gas (for example, air, nitrogen, carbon dioxide). Suitable delivery devices that may be included in the kits include the multi-compartment syringe device and/or the pressurized delivery devices described herein.

In one embodiment of the kit, a multi-compartment device is included in the kit. As previously described, the multi-compartment device may be a multiple-compartment syringe device having multiple barrels, a mixing head, and an exit orifice, wherein the dry powder composition, the first aqueous solution, and the second aqueous solution are housed separately in the multiple-compartment syringe device.

In another embodiment of the kit, a pressurized delivery device is included in the kit. As previously described, the pressurized delivery device includes a plurality of fluid component inlets each adapted to communicate with a source of different fluid components; at least one carrier fluid inlet adapted to communicate with a source of a pressurized carrier fluid; a diffuser surface located downstream from the plurality of fluid component inlets and the at least one carrier fluid inlet; and an outlet extending through the diffuser surface, wherein the diffuser surface is adapted to receive fluid components thereon and has a shape effective to direct and maintain each received fluid component in a different flow path toward the outlet for mixing and dispensing therethrough by the pressurized carrier fluid from the at least one carrier fluid inlet.

Suitable kits are not limited to the devices described herein and may also include any other suitable delivery device known in the art of drug delivery.

Uses

The surgical sealant and adhesive compositions disclosed herein can be used in a variety of different applications. In general, these compositions can be adapted for use in any tissue engineering application where synthetic gel matrices are currently being utilized. For example, the compositions are useful as tissue sealants and adhesives, vascular sealants, in tissue augmentation, in tissue repair, as hemostatic agents, and in preventing tissue adhesions, and may be used in a variety of open, endoscopic, and laparoscopic surgical procedures. One of skill in the art can easily determine the appropriate administration protocol to use with any particular composition having a known gel strength and gelation time.

In one application, the compositions described herein can be used for medical conditions that require a coating or sealing layer to prevent the leakage of gases, liquid or solids.

Methods of use typically entail applying the composition to the damaged tissue or organ to seal 1) vascular and or other tissues or organs to stop or minimize the flow of blood; 2) thoracic tissue to stop or minimize the leakage of air; 3) gastrointestinal tract or pancreatic tissue to stop or minimize the leakage of fecal or tissue contents; 4) bladder or urethra to stop or minimize the leakage of urine; 5) dura to stop or minimize the leakage of cerebrospinal fluid; and/or 6) skin or serosal tissue to stop the leakage of serosal fluid. These compositions may also be used to adhere tissues together such as small vessels, nerves or dermal tissue. The compositions can be used 1) by applying them to the surface of one tissue and then a second tissue may be rapidly pressed against the first tissue or 2) by bringing the tissues in close juxtaposition and then applying the compositions such that both the first and second tissues are contacted with the compositions. In addition, the compositions can be used to fill spaces in soft and hard tissues that are created by disease or surgery.

Therefore, one embodiment is a method of sealing tissue of a patient comprising the steps of: (a) providing a first component having a polymeric core substituted with nucleophilic groups (e.g., amino groups or thiol groups), a second component having a polymeric core substituted with electrophilic groups (e.g., succinimidyl groups), and L-DOPA; (b) rendering the nucleophilic and electrophilic groups reactive by exposing the first component, second component, and L-DOPA to an aqueous environment having a pH sufficient to effect reaction; and (c) placing the mixture into contact with tissue and allowing a three-dimensional matrix to form and seal the tissue.

In another embodiment, the surgical adhesive and/or sealant compositions can be applied in conjunction with an implanted medical device such that it prevents the leakage of gases, liquids or solids from the device or from the device-tissue interface. For example, following the implantation of a vascular graft (either synthetic or biological), there is often leakage of blood through the suture holes in the graft or at the interface between the graft and the tissue. The surgical adhesive and/or sealant composition disclosed herein can be applied to this area to prevent further blood leakage.

In an embodiment, a method of sealing tissue of a patient comprises: (a) dissolving a dry powder composition comprising a first component having a polymer core substituted with at least two sulfhydryl groups and a second component having a polymer core substituted with at least two sulfhydryl-reactive groups in a first aqueous solution comprising L-3,4-dihydroxyphenylalanine (L-DOPA) and having a pH of about 1 to about 5.5 to form a homogeneous solution; (b) adding a second aqueous solution having a pH of about 6 to about 11 to the homogeneous solution to form a mixture; and (c) placing the mixture into contact with a tissue surface and allowing a three-dimensional composition to form on the tissue surface.

In an embodiment, a method of sealing tissue of a patient comprises: (a) treating a tissue surface with a solution of L-DOPA to obtained a treated tissue surface; (b) dissolving a dry powder composition comprising a first component having a polymer core substituted with at least two sulfhydryl groups and a second component having a polymer core substituted with at least two sulfhydryl-reactive groups in a first aqueous solution having a pH of about 1 to about 5.5 to form a homogeneous solution; (c) adding a second aqueous solution having a pH of about 6 to about 11 to the homogeneous solution to form a mixture; and (d) placing the mixture into contact with the treated tissue surface and allowing a three-dimensional composition to form on the treated tissue surface.

EXAMPLES

Example 1

An L-DOPA-containing surgical adhesive was prepared using a 2 mL Coseal® Surgical Sealant (Baxter International) ("Coseal") kit composed of two synthetic polyethylene glycols (PEGs), a dilute hydrogen chloride solution and a sodium phosphate/sodium carbonate buffer solution. To prepare an L-DOPA solution, the syringe of the Coseal® kit containing diluted hydrochloric acid was removed, and the diluted hydrochloric acid solution was poured out of the syringe and precisely weighed. L-DOPA was added to the diluted hydrochloric acid solution in an appropriate amount to obtain an L-DOPA concentration of 3 to 5 mg/g of solution. For the adhesion experiments described below, the mass of the solution was 498.9 mg and the mass of L-DOPA was 1.6 mg, corresponding to an L-DOPA concentration of 3.2 mg/g. After the L-DOPA powder was completely dissolved, the solution was aspirated back into the syringe, which was then placed back in the syringe holder device.

To assess adhesion of the L-DOPA-containing surgical adhesive on a wet surface, the Coseal® sealant with added L-DOPA (referred to as "Coseal DOPA (+)") and unmodified Coseal® (referred to as "Coseal DOPA (−)") were applied to dry and wet areas of a slice of beef liver. The slice of liver was set on the bench and an area was defined for application of Coseal DOPA (+) and Coseal DOPA (−) onto wet and dry surfaces in a 2×2 matrix as shown in FIG. 2.

Figure 2:
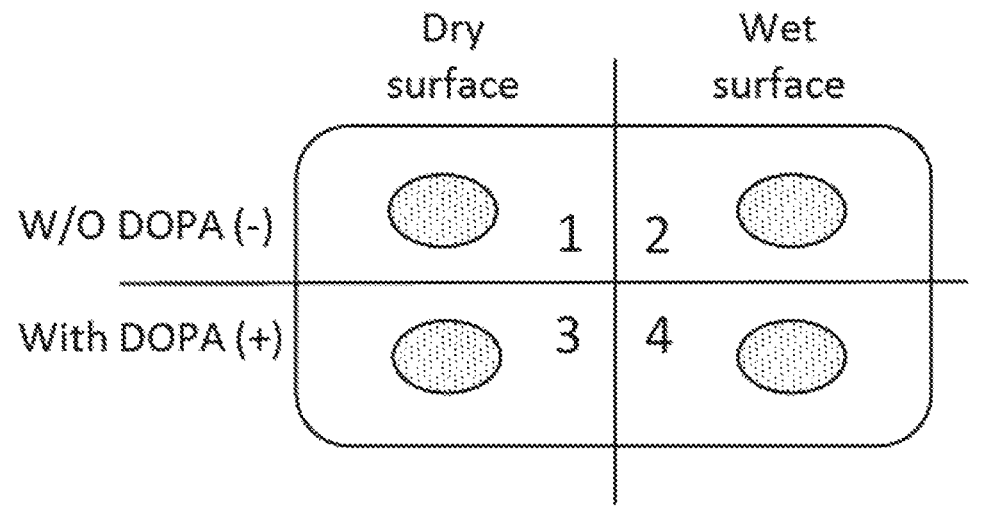

Half of the area (quadrants 2 and 4, as shown in FIG. 2) were wetted with distilled water while avoiding contamination and wetting of the dry areas (quadrants 1 and 3, as shown in FIG. 2). Excess water was removed by hanging the slice of liver vertically for a few seconds. Equal volumes of Coseal DOPA (+) and (−) were then applied onto the wet and the dry areas of the slice of liver. The applied adhesives were allowed to polymerize for a minimum of 5 minutes.

Figure 3A:
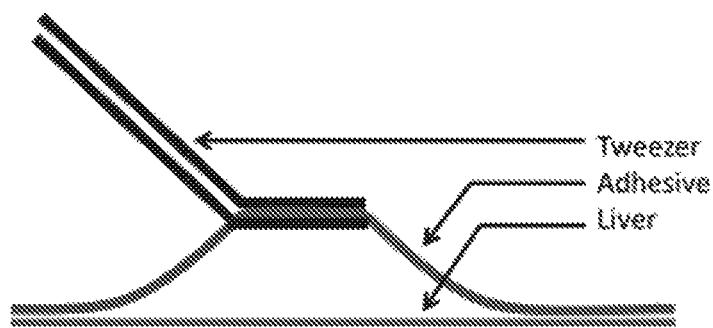
FIG. 3A is a schematic drawing of an adhesive layer demonstrating poor adhesion to a liver surface.
Figure 3B:
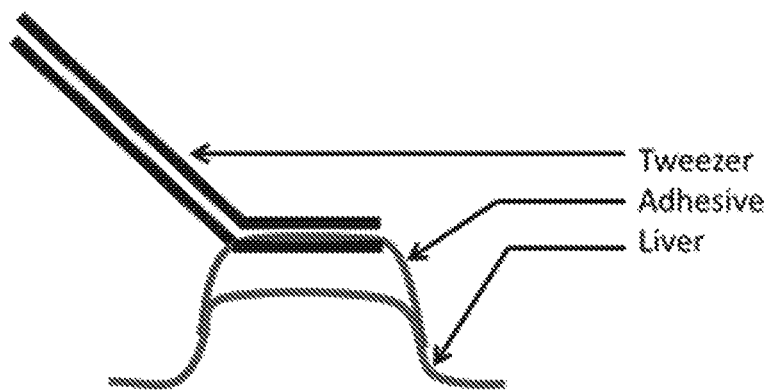
FIG. 3B is a schematic drawing of an adhesive layer demonstrating strong adhesion to a liver surface.

The adhesiveness of Coseal DOPA (+) and (−) under dry and wet conditions was assessed by using tweezers to peel off and lift up the polymerized adhesive layer. The tweezers were gently introduced between the liver and the adhesive layer and lifted to assess the adhesiveness of the adhesive layer on the liver surface as shown in FIGS. 3A and 3B. The results of the adhesiveness assessment are shown in FIG. 4A (Coseal DOPA (−) applied on dry surface), FIG. 4B (Coseal DOPA (+) applied on dry surface), FIG. 4C (Coseal DOPA (−) applied on wet surface), and FIG. 4D (Coseal DOPA (+) applied on wet surface).

Figure 4A:
FIG. 4A is a photograph of Coseal DOPA (−) applied on a dry surface.
Figure 4B:
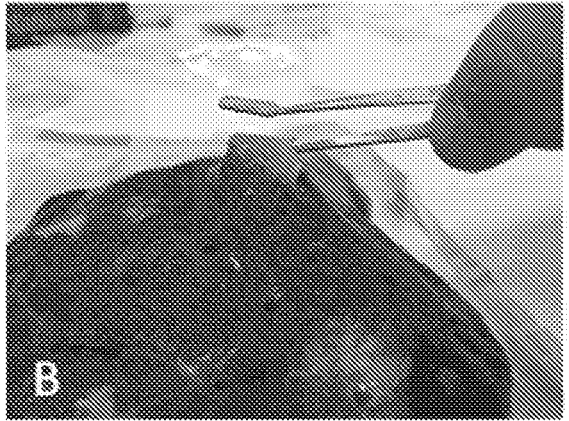
FIG. 4B is a photograph of Coseal DOPA (+) applied on a dry surface.
Figure 4C:
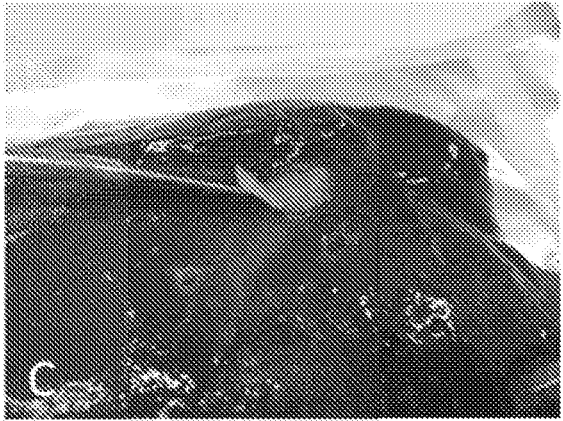
FIG. 4C is a photograph of Coseal DOPA (−) applied on a wet surface.
Figure 4D:
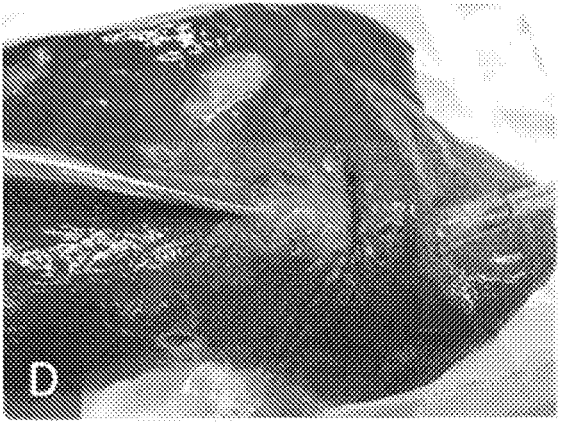
FIG. 4D is a photograph of Coseal DOPA (+) applied on a wet surface.

As shown in FIG. 4A, Coseal DOPA (−) demonstrated adhesion to a dry surface, with the adhesive material being only partially torn apart from the liver surface while some material remained on the liver tissue. As shown in FIG. 4C, Coseal DOPA (−) demonstrated poor adhesion to a wet surface, with the adhesive layer being lifted up and removed from the surface. As shown in FIG. 4B and FIG. 4D, Coseal DOPA (+) advantageously demonstrated adhesion to both dry and wet surfaces, in particular demonstrating significantly improved adhesion to wet surfaces.

Example 2

The adhesion of unmodified Coseal® surgical sealant to a surface treated with a spray of an L-DOPA solution was assessed according to the following procedure. An L-DOPA solution was prepared by dissolving about 6 mg of L-DOPA in 2 mL of water, and then aspirating the solution into a syringe. Coseal® surgical sealant was prepared according to the manufacturer's instructions. A slice of beef liver was divided into two areas: a dry area and a wet area that was wetted and thereby "primed" with the L-DOPA solution using a 21G needle. Equal volumes of Coseal® were then applied to the dry area and to the area having been treated with the L-DOPA solution. The applied adhesive was allowed to cure for 5 minutes.

The adhesiveness was then assessed by using tweezers to peel off and lift up the polymerized adhesive layers. The tweezers were gently introduced between the liver and the adhesive layer and lifted to assess the adhesiveness of the adhesive layer on the liver surface. The results of the adhesiveness assessment are shown in FIG. 5A (dry surface) and FIG. 5B (surface wetted with L-DOPA).

Figure 5A:
FIG. 5A is a photograph of Coseal DOPA (−) applied on a dry surface.
Figure 5B:
FIG. 5B is a photograph of Coseal DOPA (−) applied on a surface wetted with L-DOPA solution.

As shown in FIG. 5A and FIG. 5B, Coseal® demonstrated significantly improved adhesion when applied to a surface that had been treated with an L-DOPA solution compared to a dry surface.

The present invention is described in connection with preferred embodiments. However, it should be appreciated that the invention is not limited to the disclosed embodiments. It is understood that, given the description of the embodiments of the invention herein, various modifications can be made by a person skilled in the art. Such modifications are encompassed by the claims below.

What is claimed is:

1. A system comprising:
   a multi-chamber syringe assembly comprising:
   a first syringe;
   a second syringe;
   a syringe housing having two first orifices at a first end and two second orifices at a second end, the syringe housing holding both the first syringe and the second syringe in parallel so that outlets of both the first syringe and the second syringe extend through the first orifices of the first end of the syringe housing and a first plunger of the first syringe and a second plunger of the second syringe extend through the second orifices of the syringe housing;
   a syringe clip coupled to the first plunger of the first syringe and the second plunger of the second syringe;
   a transfer port closure adapter having two first inlets at a third end and one second inlet at a fourth end, the third end of the transfer port closure adapter configured to be attached to the first end of the syringe housing so that the outlets of both the first syringe and the second syringe are adapted to the two first inlets of the transfer port closure adapter; and a third syringe with its outlet adapted to the second inlet of the transfer port closure adapter;
a first aqueous solution having a pH of about 1 to about 5.5 in the first syringe;
a second aqueous solution having a pH of about 6 to about 11 in the second syringe;
a dry powder composition comprising a first component having a polymer core substituted with at least two sulfhydryl groups and a second component having a polymer core substituted with at least two sulfhydryl-reactive groups in the third syringe.

2. The system of claim 1, wherein the syringe clip is uncoupable from either the first plunger or the second plunger.

3. The system of claim 1, wherein the transfer port closure adapter allows contents of the first syringe, the second syringe and the third syringe to be selectively mixed.

4. The system of claim 1, wherein the third syringe and transfer port closure adapter are detached from the multi-chamber syringe assembly.

5. The system of claim 4, wherein the outlets of both the first syringe and the second syringe of the multi-chamber syringe assembly are stopped by an applicator.

6. The system of claim 1, wherein the first aqueous solution further comprises L-3,4-dihydroxyphenylalanine (L-DOPA).

7. The system of claim 1, wherein the first component polymer core and second component polymer core are both branched poly (ethylene oxide).

8. The system of claim 1, wherein the sulfhydryl-reactive groups are succinimidyl groups.

9. The system of claim 1, wherein the dry powder composition comprises a 4-arm, succinimidyl-terminated poly (ethylene oxide) and a 4-arm, thiol-terminated poly (ethylene oxide).

10. The system of claim 1, wherein the dry powder composition comprises an 8-arm, succinimidyl-terminated poly(ethylene oxide) and an 8-arm, thiol-terminated poly (ethylene oxide).

11. The system of claim 1, wherein the dry powder composition comprises (i) an 8-arm, succinimidyl-terminated poly(ethylene oxide) and a 4-arm, thiol-terminated poly(ethylene oxide); or (ii) a 4-arm, succinimidyl-terminated poly(ethylene oxide) and an 8-arm, thiol-terminated poly(ethylene oxide).

12. The system of claim 1, wherein the first component is

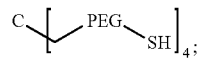

wherein PEG is poly(ethylene oxide).

13. The system of claim 1, wherein the second component is

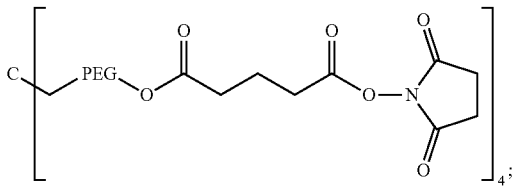

wherein PEG is poly(ethylene oxide).

14. The system of claim 1, wherein the system produces a surgical adhesive or sealant composition comprising a crosslinked polymeric material having a structure:

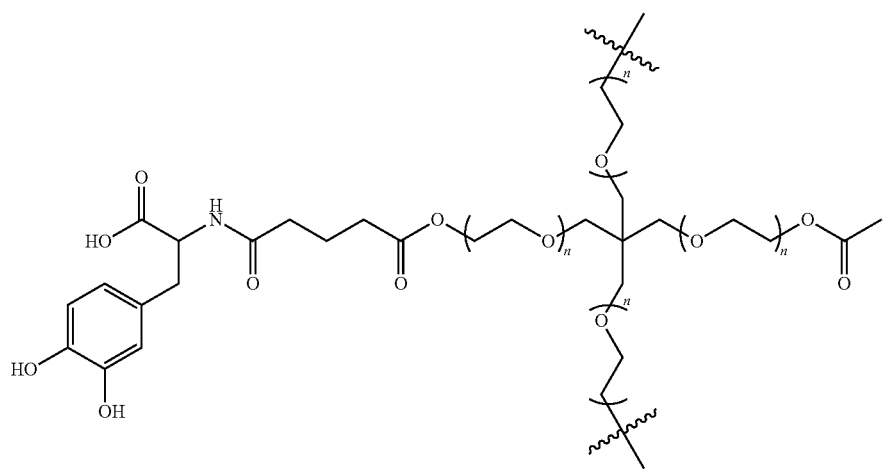

-continued
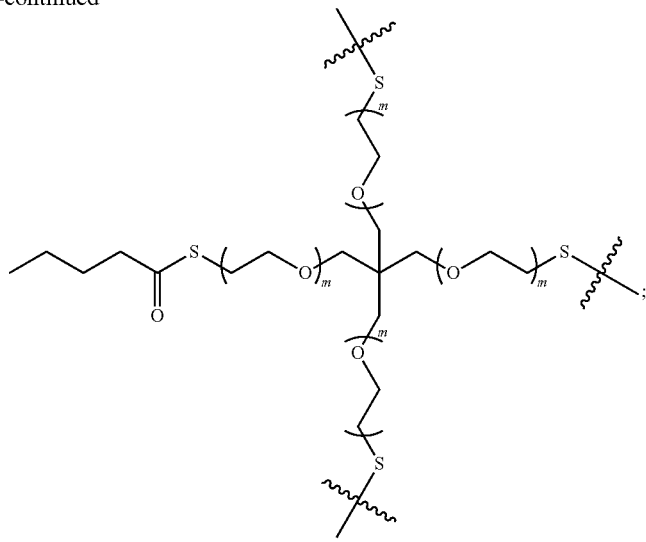
wherein each n is independently 15 to 150; and each m is independently 15 to 150.
15. A method of using the system of claim 1 to produce a surgical adhesive or sealant composition.
* * * * *